(12) United States Patent
Igarashi

(10) Patent No.: US 6,402,685 B1
(45) Date of Patent: Jun. 11, 2002

(54) FIELD CONVERSION SYSTEM FOR RIGID ENDOSCOPE

(75) Inventor: Tsutomu Igarashi, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/358,936

(22) Filed: Jul. 23, 1999

Related U.S. Application Data

(62) Division of application No. 09/057,337, filed on Apr. 9, 1998, now Pat. No. 5,954,634.

(30) Foreign Application Priority Data

Apr. 11, 1997 (JP) ............................................. 9-094002

(51) Int. Cl.⁷ ............................................. A61B 1/055
(52) U.S. Cl. ....................... 600/111; 600/168; 600/173; 600/109
(58) Field of Search ................... 600/166, 111, 600/112, 109, 168, 181; 348/45

(56) References Cited

U.S. PATENT DOCUMENTS

| 5,577,991 A | | 11/1996 | Akui et al. |
| 5,720,706 A | * | 2/1998 | Takahashi et al. ........... 600/111 |
| 5,743,846 A | | 4/1998 | Takahashi et al. |
| 5,743,847 A | * | 4/1998 | Nakamura et al. ........... 600/111 |
| 5,776,049 A | * | 7/1998 | Takahashi ..................... 600/111 |
| 5,864,359 A | * | 1/1999 | Kazakevich ................. 600/111 |
| 5,964,696 A | * | 10/1999 | Mihalca et al. .............. 600/111 |

FOREIGN PATENT DOCUMENTS

| JP | 8-332169 | 12/1996 |
| JP | 9-28663 | 2/1997 |

\* cited by examiner

Primary Examiner—John P. Leubecker
(74) Attorney, Agent, or Firm—Pillsbury Winthrop LLP

(57) ABSTRACT

A field conversion system for rigid endoscopes has a rigid endoscope inserted into an object to form an optical image of the object and an imaging device connected to the rigid endoscope. The imaging device includes an imaging optical system for changing the magnification of the optical image to form a resultant image and an image sensor placed at the position of an imaging plane produced by the imaging optical system. A part or a whole of the imaging optical system or the image sensor is moved in a direction perpendicular to an optical system, thereby carrying out a field conversion. The field conversion system is provided with a time-division shutter mechanism placed close to a pupil position inside the imaging optical system so that two light beams at different positions in a pupil are switched time-dividedly and transmitted and the image sensor picks up time-dividedly left and right images with parallax.

5 Claims, 6 Drawing Sheets

FIELD CONVERSION SYSTEM FOR RIGID ENDOSCOPE

This is a division of application Ser. No. 09/057,337, filed Apr. 9 1998, now U.S. Pat. No. 5,954,634.

BACKGROUND OF THE INVENTION

1. Field of the Invention

This invention relates to a field conversion system for rigid endoscopes which are used in the fields of medicine and industry and are inserted into cavities inside a human body and a pipe so that an object part can be observed by an external display.

2. Description of Related Art

As an example of a surgical operation, a method is known that a rigid endoscope is inserted into a human body to display an affected part on the image screen of a TV monitor or the like, and an operator manipulates, by remote control, various treatment tools, such as a suture instrument, electric knife, and cavitron ultrasonic surgical aspirator, inserted into the human body independently of the endoscope, while observing the image screen to treat the affected part. Where such methods are applied to various treatments, it is desirable that the affected part to be treated is displayed at a nearly middle position of the monitor screen and with the size of an image the operator desires. Thus, in order to enable the operator to devote himself exclusively to the treatment, a scope holding assistant has been adopted in addition to the operator. The scope holding assistant has manipulated the rigid endoscope in response to the oral instructions of the operator to adjust the direction and position of the rigid endoscope being inserted and to control the movement of a visual field and the size of the image.

In this case, however, there are problems that a full-time scope holding assistant must be adopted and that because a cooperation between the operator and the assistant is difficult, work efficiency is impaired and the operator may be irritated according to circumstances. Thus, in order to solve these problems, field conversion systems for rigid endoscopes using conventional, optical trimming techniques are proposed by Japanese Patent Preliminary Publication Nos. Hei 8-332169 and Hei 9-28663. According to these publications, it becomes possible that the operator carries out a field conversion by himself without virtually affecting the manipulation of the treatment tools.

Each of the above publications, however, fails to disclose specific means for solving the following three problems encountered when the field conversion is made. The first problem refers to optical interchangeability with an existing observation system for rigid endoscopes. The observation system for rigid endoscopes which already has widespread use is designed so that the rigid endoscope is provided to be independent of an imaging device and a combination of both can be arbitrarily changed to make observations. However, where the change of this combination is made possible, each of the publications does not set forth the arrangement of an optical system capable of effectively performing the function of the field conversion.

The second problem refers to the relationship of performance between a rigid endoscope and an image sensor. In order to make a magnified image observable with good image quality, it is necessary to use a rigid endoscope of high image quality having the amount of information several times that of the image sensor. In this case, the amount of information which can be transmitted in a wide-angle condition is restricted by that of the image sensor. Thus, If an image sensor with a small amount of information is used, the performance of the rigid endoscope of high image quality will not be optimized. Each of the above publications fails to set forth means for overcoming this difficulty.

The third problem relates to a stereoscopic observation. Recently, with the advent of a rigid endoscope for stereoscopy, the remote control of treatment tools with stereoscopy has been intended. Each publication, however, does not disclose a specific construction such that the field conversion and the stereoscopy are compatible with each other.

SUMMARY OF THE INVENTION

It is, therefore, a primary object of the present invention to provide a field conversion system for rigid endoscopes in which even when a combination of the rigid endoscope and the imaging device is varied, an image size required for the field conversion is obtained with respect to the rigid endoscope and the imaging device.

It is another object of the present invention to provide a field conversion system for rigid endoscopes which has an imaging device capable of optimizing the image quality of the rigid endoscope.

It is still another object of the present invention to provide a field conversion system for rigid endoscopes which has an imaging device in which the field conversion and the stereoscopy are compatible with each other.

In order to achieve these objects, according to one aspect of the present invention, the field conversion system for rigid endoscopes includes a rigid endoscope inserted into an object to be observed, from one end thereof in a longitudinal direction to form an optical image of the object and an imaging device connected to the other end thereof. The imaging device has an imaging optical system for changing the magnification of the optical image to form a resultant image and an image sensor placed at the position of an imaging plane produced by the imaging optical system. In this way, a part or the whole of the imaging optical system, or the image sensor is moved in a direction perpendicular to the optical axis, and thereby the field conversion is carried out. The rigid endoscope includes, in order from the side of the one end thereof, an objective optical system, a relay optical system, and an eyepiece optical system, and is constructed so that the relay optical system forms an image on the side of the other end thereof. The field conversion system satisfies the following conditions:

$$0.6 \leq Dm|fw/foc|/Lc \leq 1.2 \tag{1}$$

$$1.6 \leq Dm|ft/foc|/Lc \leq 4 \tag{2}$$

where Dm is the size of the image formed by the relay optical system, Lc is the diagonal length of an effective imaging surface of the image sensor, foc is the focal length of the eyepiece optical system, fw is the focal length of the imaging optical system at a low magnification position, and ft is the focal length of the imaging optical system at a high magnification position.

According to another aspect of the present invention, the field conversion system for rigid endoscopes includes a rigid endoscope inserted into an object to be observed, from one end thereof in a longitudinal direction to form an optical image of the object and an imaging device connected to the other end thereof. The imaging device has an imaging optical system for forming the optical image and an image sensor placed at the position of an imaging plane produced by the imaging optical system. In this way, all or a part of image information derived from the image sensor is selectively displayed on a monitor to thereby perform the field conversion and magnify or demagnify the image. The rigid endoscope includes, in order from the side of the one end thereof, an objective optical system, a relay optical system, and an eyepiece optical system, and is constructed so that the relay optical system forms an image on the side of the other end thereof. The number of pixels of the image sensor is at least one million, and the field conversion system satisfies the following condition:

$$0.6 \leq Dm|fi/foc|/Lc \leq 1.2 \qquad (3)$$

where fi is the focal length of the imaging optical system.

According to still another aspect of the present invention, the field conversion system for rigid endoscopes includes a rigid endoscope inserted into an object to be observed, from one end thereof in a longitudinal direction to form an optical image of the object and an imaging device connected to the other end thereof. The imaging device has an imaging optical system for changing the magnification of the optical image to form a resultant image and an image sensor placed at the position of an imaging plane produced by the imaging optical system. In this way, a part or the whole of the imaging optical system, or the image sensor is moved in a direction perpendicular to the optical axis, and thereby the field conversion is carried out. A time-division shutter mechanism is placed close to a pupil position in the imaging optical system so that two light beams at different positions in the pupil are switched time-dividedly and transmitted and the image sensor picks up time-dividedly left and right images with parallax.

According to a further aspect of the present invention, the field conversion system for rigid endoscopes includes a rigid endoscope inserted into an object to be observed, from one end thereof in a longitudinal direction to form an optical image of the object and an imaging device connected to the other end thereof. The imaging device has an imaging optical system for forming the optical image and an image sensor placed at the position of an imaging plane produced by the imaging optical system. In this way, all or a part of image information derived from the image sensor is selectively displayed on a monitor to thereby perform the field conversion and magnify or demagnify the image. The number of pixels of the image sensor is at least one million, and a time-division shutter mechanism is placed close to a pupil position in the imaging optical system so that two light beams at different positions in the pupil are switched time-dividedly and transmitted and the image sensor picks up time-dividedly left and right images with parallax.

These and other objects as well as the features and advantages of the present invention will become apparent from the following detailed description of the preferred embodiments when taken in conjunction with the accompanying drawings.

DETAILED DESCRIPTION OF THE PREFERRED EMBODIMENTS

Figure 1:
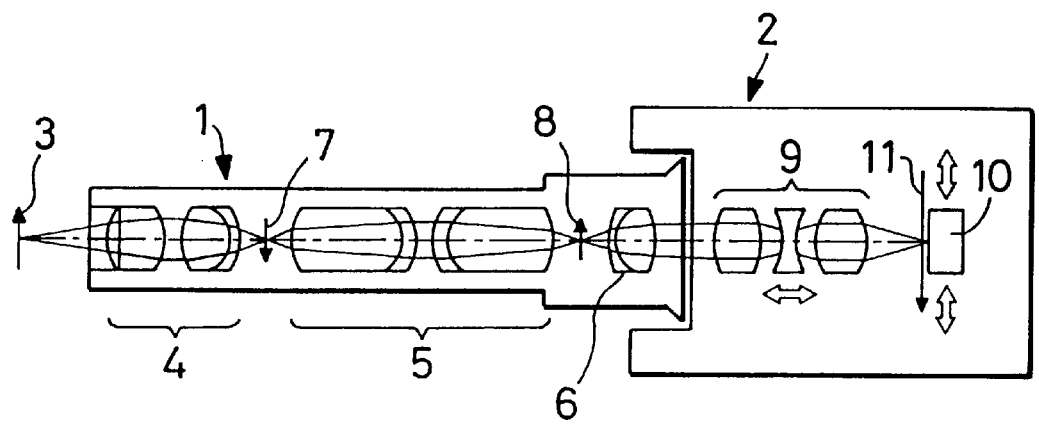
FIG. 1 is a view showing the entire construction of the field conversion system for rigid endoscopes of a first embodiment in the present invention.

In accordance with the embodiments shown in the drawings, the present invention will be explained below. Now, the first embodiment is described with reference to FIGS. 1, 2A–2D, and 3A–3D. A rigid endoscope 1 in the first embodiment, as is well known, is designed so that an elongated, cylindrical portion can be inserted into the human body, from one end of the rigid endoscope 1 shown in FIG. 1, and the other end is connected to an imaging device 2. The rigid endoscope 1 and the imaging device 2 can be disconnected from each other and have a mount system in common. It is thus possible that another imaging device is connected to the rigid endoscope 1, or another rigid endoscope is connected to the imaging device 2. The rigid endoscope 1 includes, in order from the side of an object 3 to be observed, an objective optical system 4, a relay optical system 5, and an eyepiece optical system 6. The relay optical system 5 is designed to transmit, at least once, an image 7 formed by the objective optical system 4 and to form an image 8 on the side of the other end of the rigid endoscope 1. The eyepiece optical system 6 is adapted to change a diopter so that the image 8 can be visually observed. Also, although, as is well known, an illumination optical system is placed, in addition to an observation optical system such as that mentioned above, inside the rigid endoscope 1, it has no direct bearing upon the present invention and thus is omitted from the figure and the description.

The imaging device 2 has an imaging optical system 9 including a zoom lens unit and an image sensor 10. The imaging optical system 9 is constructed so that a light beam from the eyepiece optical system 6 is transmitted to form a rigid-endoscope image 11 on the imaging surface of the image sensor 10. The field conversion is made by holding the imaging optical system 9 fixed on the optical axis thereof to move the image sensor 10 in a direction perpendicular to the optical axis along the imaging plane. The rigid-endoscope image 11 which has been picked up is displayed as a picture on a TV monitor, not shown, in a conventional way. The movement of the image sensor 10, as set forth in each of the prior art publications, is conducted in such a way that a control switch (for example, a foot control switch) is operated to control an actuator and the image sensor 10 is brought to a desired position through an XY stage.

For this construction of the first embodiment, in order that an image of proper size is displayed on the TV monitor when the imaging optical system 9 including a zoom lens unit is situated at the low magnification position, it is necessary to satisfy the condition of Eq. (1) already mentioned. Also, where a field mask is placed at the position of the image 8 of the relay optical system 5, the image size Dm stands for the inside diameter of the field mask.

The term|fw/foc| of Eq. (1) implies a magnification obtained by a combination of the eyepiece optical system 6 and the imaging optical system 9 at the low magnification position. The term Dm|fw/foc| means the size of the rigid-endoscope image 11 projected on the imaging plane at the low magnification position. Hence, the value of this term divided by the diagonal length Lc of the effective imaging surface of the image sensor 10 becomes a parameter representing the size of the rigid-endoscope image displayed on the monitor at the low magnification position. In the following explanation, the calculation value of Dm|fw/foc|/Lc is referred to as "the value of Eq. (1)".

Using now FIGS. 2A–2D, a description is given of the size of the image displayed on an image screen T of the TV monitor, governed by the value of Eq. (1). In each of these figures, it is assumed that the shape of the rigid-endoscope image 11 (the visual field of the rigid endoscope 1) is circular, the effective imaging surface of the image sensor 10 has the shape of a rectangle whose aspect ratio is 3:4, and the image screen T of the TV monitor has a similar figure with respect to the effective imaging surface of the image sensor 10. It is also assumed that the function of the field conversion is not exerted and the optical system is in a condition that it is not decentered from the optical axis. On the image screen T, an affected part to be cut out and scissors for the treatment tool are displayed.

Figure 2A:
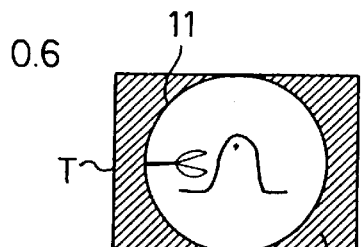
FIGS. 2A. 2B, 2C, and 2D are views showing that the relationship between a rigid-endoscope image in an imaging plane and an effective area of an image sensor varies with a condition at the low magnification position.
Figure 2B:
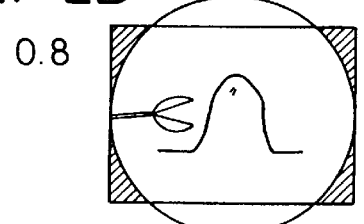
Figure 2C:
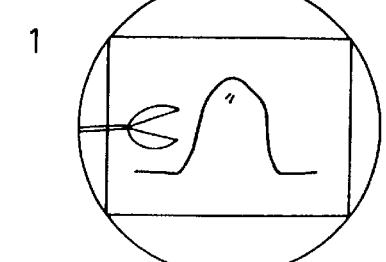
Figure 2D:
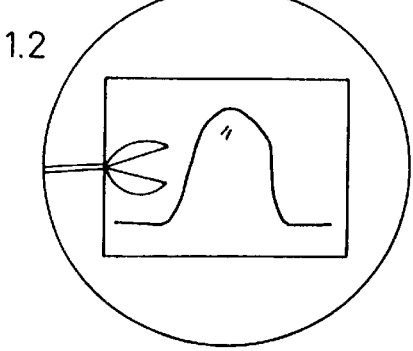

FIG. 2A shows the case where the value of Eq. (1) is 0.6. In this figure, the upper and lower edges of the image screen T of the TV monitor coincide with the periphery of the visual field of the rigid endoscope. FIG. 2B shows the case where it is 0.8. In this figure, the left and right edges of the image screen T coincide with the periphery. FIG. 2C shows the case where it is 1. In this figure, the diagonal ends of the image screen T coincide with the periphery. FIG. 2D shows the case where it is 1.2. In this figure, the periphery ceases to be visible on the image screen T.

When the imaging optical system 9, namely the zoom lens unit, is situates at the low magnification position, the image screen T is adapted to display the image for the main purpose of looking out over the entire area of the visual field of the rigid endoscope 1, and thus it is desirable that the rigid-endoscope image 11 can be displayed in the widest possible range. For this reason, if the value of Eq. (1) is extremely large, the visual field becomes narrow, which raises a problem. Thus, the condition of FIG. 2D means a limit to image display, and it is unfavorable that the rigid-endoscope image 11 is further magnified. If, on the other hand, the value of Eq. (1) is extremely small, a dark portion D on the image screen T will increase, with a resulting difficulty in observation. Although the condition of FIG. 2A is such that the rigid-endoscope image 11 can be viewed over the entire area, this condition means a limit to image display, and it is unfavorable that the image 11 is further demagnified. From the above description, it is considered that the image display on the image screen T an observer desires, at the low magnification position, is limited to the conditions of FIGS. 2B and 2C, and the conditions of FIGS. 2A and 2D indicate the lower and upper limits, respectively, of the size of the rigid-endoscope image 11. In this way, it becomes necessary to satisfy Eq. (1).

For the first embodiment, on the other hand, in order to display an image of proper size on the TV monitor when the imaging optical system 9 of the zoom lens unit is situated at the high magnification position, it is necessary to satisfy the condition of Eq. (2) already mentioned. Also, where a field mask is placed at the position of the image 8 of the relay optical system 5, the image size Dm stands for the inside diameter of the field mask.

The term|ft/foc| of Eq. (2) implies a magnification obtained by a combination of the eyepiece optical system 6 and the imaging optical system 9 at the high magnification position. The term Dm|ft/foc| means the size of the rigid-endoscope image 11 projected on the imaging plane at the high magnification position. Hence, the value of this term divided by the diagonal length Lc of the effective imaging surface of the image sensor 10 becomes a parameter representing the size of the rigid-endoscope image displayed on the monitor at the high magnification position. In the following explanation, the calculation value of Dm|ft/foc|/Lc is referred to as "the value of Eq. (2)".

Figure 3A:
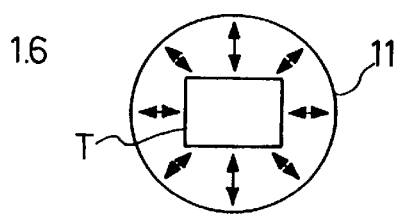
FIGS. 3A. 3B, 3C, and 3D are views showing that the relationship between the rigid-endoscope image in the imaging plane and the effective area of the image sensor varies with a condition at the high magnification position.
Figure 3B:
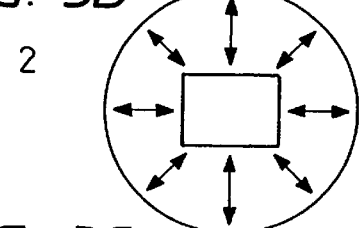
Figure 3C:
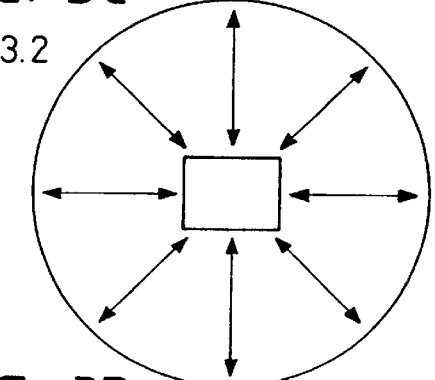
Figure 3D:
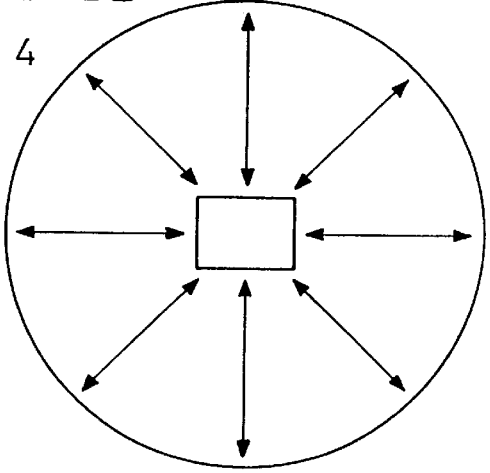

Using now FIGS. 3A–3D, a description is given of the size of the image displayed on a image screen T of the TV monitor, governed by the value of Eq. (2). In these figures, the shape of the rigid-endoscope image 11 (the visual field of the rigid endoscope 1), the aspect ratio of the effective imaging surface of the image sensor 10, and the relation with the image screen T of the monitor are the same as those in FIGS. 2A–2D. FIG. 3A shows the case where the value of FIG. (2) is 1.6. In this figure, a point where a length from the optical axis to either the left or right edge of the image screen T of the TV monitor is extended twice coincides with the periphery of the visual field of the rigid endoscope. FIG. 3B shows the case where it is 2. In this figure, a point where a length from the optical axis to any one of the diagonal ends of the image screen T is extended twice coincides with the periphery. FIG. 3C shows the case where it is 3.2. In this figure, a point where a length from the optical axis to either the left or right edge of the image screen T is extended four times coincides with the periphery. FIG. 3D shows the case where it is 4. In this figure, a point where a length from the optical axis to any one of the diagonal ends of the image screen T is extended four times coincides with the periphery.

When the imaging optical system 9, namely the zoom lens unit, is situated at the high magnification position, the image screen T is adapted to optimize the function of the field conversion. For this reason, if the value of Eq. (2) is extremely small, the meaning of carrying out the field conversion will be lost. For example, if the condition of FIG. 2D mentioned above is brought about, the rigid-endoscope image existing outside the imaging surface will be diminished, and hence this condition will no longer be on a level that the field conversion is carried out. Thus, although a condition such that two imaging surfaces are obtained in a horizontal direction, without overlapping, with respect to the rigid-endoscope image is shown in FIG. 3A, there is no sense unless the rigid-endoscope image is formed at this level even in the worst case.

Conversely, if the value of Eq. (2) is extremely large, inconvenience will be caused to functions excluding that of the field conversion. Specifically, where the rigid-endoscope image is very highly magnified, as is well known, a reduction in illumination on the imaging surface becomes pronounced and the image displayed on the monitor screen will be hard to see. Another problem is that since it is required that the focal length of the imaging optical system 9 is increased to heighten a variable magnification ratio, the imaging device 2 becomes oversized. In FIG. 3D, a limit condition according to these reasons is shown. The size of the rigid-endoscope image in this condition is such that the function of the field conversion can be completely exerted. However, since its brightness is 0.16 times that of the case of FIG. 3A and the focal length of the imaging optical system 9 is 2.5 times, it is unfavorable that the image is further magnified. From the above description, it is considered that the conditions of FIGS. 3B and 3C are favorable for the size of the rigid-endoscope image at the high magnification position, and the conditions of FIGS. 3A and 3D set the lower and upper limits, respecitively, of the size of the rigid-endoscope image 11. In this way, it becomes necessary to satisfy Eq. (2).

The following tables give numerical data of the optical systems applied to the first embodiment. In these tables, R1–R6 stand for six kinds of samples of the rigid-endoscope optical system, Z1 and Z2 stand for two kinds of samples of the imaging optical system with the zoom lens unit, $\theta$ denotes an angle of view, and NA denotes the numerical aperture of emergence of the relay optical system 5. Other symbols are the same as those used in Eqs. (1) and (2).

| | Rigid endoscope | | | | |
|---|---|---|---|---|---|
| | Dm (mm) | foc (mm) | $\theta$ (°) | NA | NA Dm |
| R1 | 7 | 28.5 | 80 | 0.12 | 0.84 |
| R2 | 7 | 22.0 | 100 | 0.05 | 0.35 |
| R3 | 4.4 | 17.7 | 70 | 0.1 | 0.44 |
| R4 | 5.5 | 31.0 | 60 | 0.055 | 0.30 |
| R5 | 6 | 21.2 | 120 | 0.1 | 0.60 |
| R6 | 7.2 | 34.0 | 80 | 0.1 | 0.72 |

| | Imaging optical system | | |
|---|---|---|---|
| | Lc (mm) | fw (mm) | ft (mm) |
| Z1 | 4.56 | 16.9 | 41.3 |
| Z2 | 3.07 | 10.5 | 37.6 |

| | Values of Eqs. (1) and (2) | | | |
|---|---|---|---|---|
| | Combination with Z1 | | Combination with Z2 | |
| | Eq. (1) | Eq. (2) | Eq. (1) | Eq. (2) |
| R1 | 0.91 | 2.22 | 0.84 | 3.01 |
| R2 | 1.18 | 2.88 | 1.09 | 3.90 |
| R3 | 0.92 | 2.25 | 0.85 | 3.04 |
| R4 | 0.66 | 1.61 | 0.61 | 2.17 |
| R5 | 1.05 | 2.56 | 0.97 | 3.47 |
| R6 | 0.78 | 1.92 | 0.72 | 2.59 |

Eqs. (1) and (2) in the first embodiment, as mentioned above, are defined by the entire optical construction of the rigid endoscope 1 and the imaging device 2 which are provided independently of each other for interchangeability. Thus, when a system is previously constructed so that the conditions of these two equations are satisfied at the same time, it becomes possible to effectively make the field conversion in the surgical operation using the rigid endoscope. If these conditions are even satisfied, various kinds of rigid endoscopes which are different in field direction, angle of view, shape, etc., irrespective of existing rigid endoscopes, can be used in such a way that each of them is selectively attached to a particular imaging device having the function of the field conversion, unless the rigid endoscope and the imaging device are defective in mount construction. Conversely, imaging devices of different specifications can, of course, be used in such a way that each of them is attached interchangeably to a particular rigid endoscope. Also, even when a rigid endoscope which fails to satisfy the above conditions is mounted to the imaging device 2, the imaging device 2 functions as an imaging device with a zoom lens unit and thus its application is not limited.

Figure 4A:
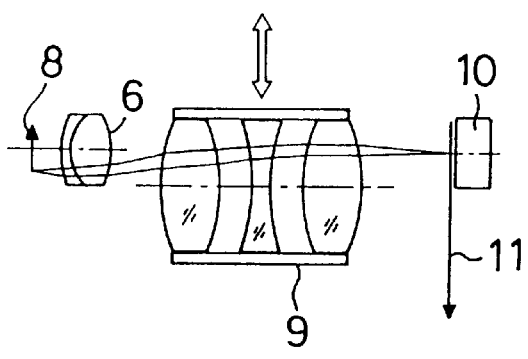
FIGS. 4A and 4B are views showing arrangements of modification examples of an imaging optical system in the first embodiment.
Figure 4B:
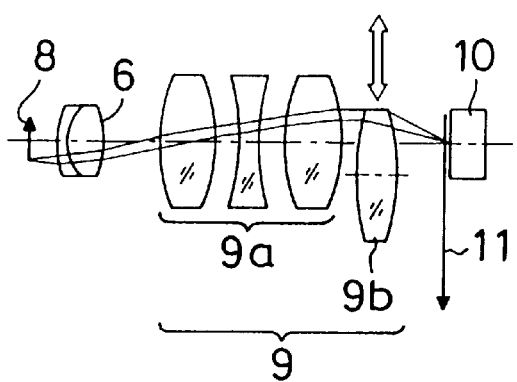

The imaging device 2 in the first embodiment, as described above, is designed so that, in order to carry out the field conversion, the optical axis of the imaging optical system 9 is fixed and the image sensor 10 is moved. However, the field conversion is possible when the positional relationship between the rigid-endoscope image 11 formed in the imaging plane and the image sensor 10 is relatively changed. Hence, even where the image sensor 10 is fixed and the whole or a part of the imaging optical system 9 is moved in a direction perpendicular to the optical axis, the same effect can be secured. FIG. 4A shows a modification example where the whole of the imaging optical system 9 is moved in this a way. FIG. 4B shows another example where the imaging optical system 9 includes a zoom lens unit 9a and a lens unit 9b so that only the lens unit 9b is moved.

Figure 5:
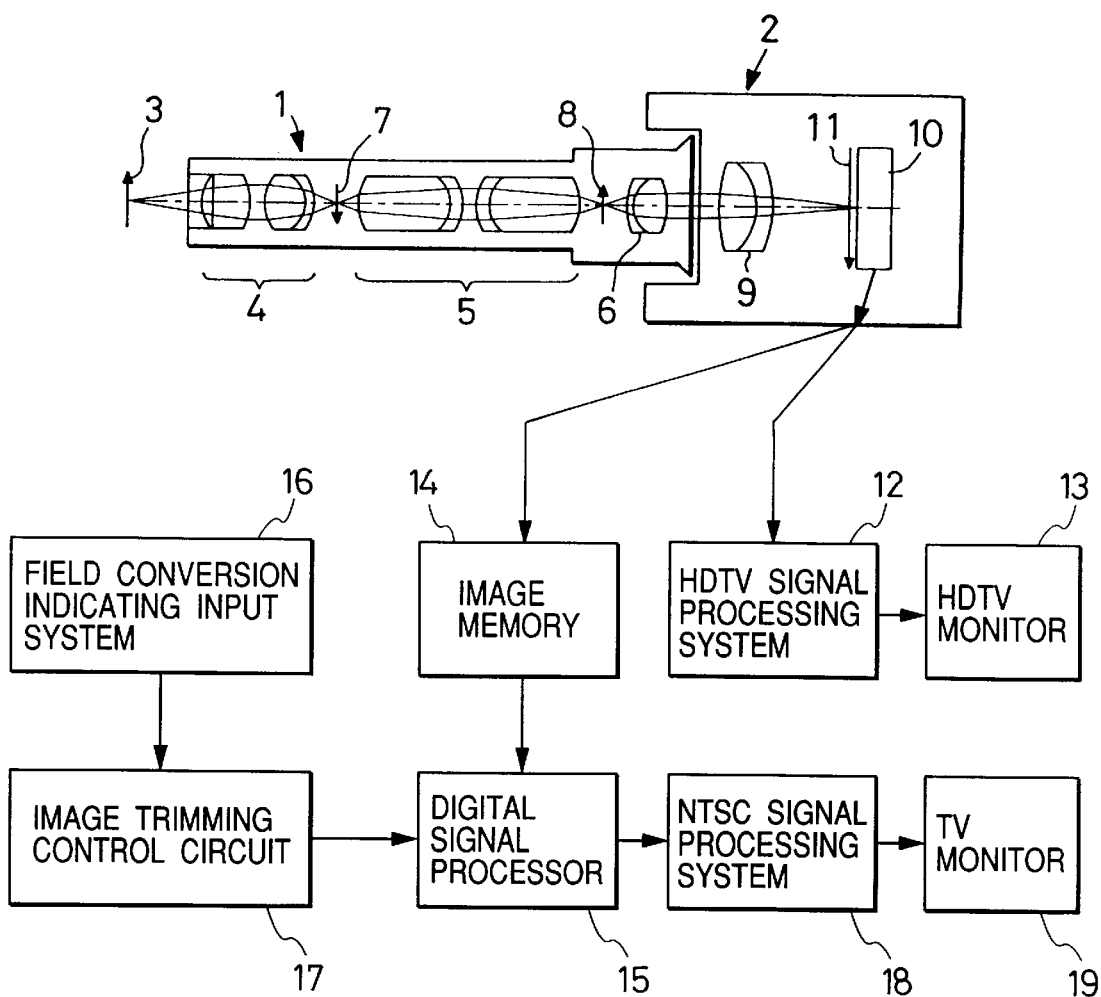
FIG. 5 is a view showing the entire construction of the field conversion system for rigid endoscopes of a second embodiment in the present invention.

Subsequently, the second embodiment is explained with reference to FIG. 5. Since the construction of the rigid endoscope 1 is exactly the same as that of the first embodiment shown in FIG. 1, like numerals are used in like members and its detailed explanation is omitted. The optical construction of the imaging device 2 is also the same in arrangement as FIG. 1 and thus numerals identical with those in the first embodiment are conveniently used. However, the imaging optical system 9 in the second embodiment has no zoom lens unit, and the imaging optical system 9 and the image sensor 10 are both fixed so that they are not moved when the field conversion is made. The image sensor 10 in the second embodiment has one million or more pixels.

The second embodiment is constructed so that where full image information of the rigid-endoscope image 11 derived from the image sensor 10 is displayed, an image signal from the image sensor 10, after being converted into that of a high-resolution standard by an HDTV signal processing system 12, is outputted to an HDTV monitor 13. On the other hand, where the field conversion is carried out, the image signal from the image sensor 10 is previously stored in an image memory 14 so that partial image trimming is performed by a digital signal processor 15. Subsequently, when an operator controls a field conversion indicating input system 16 to issue instructions for the field conversion, the actuation of an image trimming control circuit 17 causes the digital signal processor 15 to perform the trimming of an indicated area so that partial image information thereof is outputted to an NTSC signal processing system 18. In this way, the NTSC signal processing system 18 forms an input signal into an NTSC-grade image signal to display an image on a TV monitor 19.

In the second embodiment, the fact that the number of pixels of the image sensor is limited to at least one million lies for the purpose of causing an electrically trimmed image to have an NTSC-grade image quality. Since, as is well known, the amount of information of a partial image which is electrically trimmed is smaller than that of full image information, a displayed image has poor resolution. However, the number of pixels of the image sensor used at present In NTSC is on the order of 250,000 to 400,000, and thus the amount of information corresponding to about 250,000 pixels is satisfactory for image trimming. Thus, if a simple calculation is made irrespective of the aspect ratio of the image sensor, four images, each having the amount of information corresponding to 250,000 pixels, will be derived, without overlapping, from the image sensor with one million pixels. In general, at least, such a degree of ratio is required for carrying out the field conversion of the rigid-endoscope image. Hence, if the image sensor with at least one million pixels is provided as in the second embodiment, the trimmed image of the amount of information corresponding to at least 250,000 pixels will be obtained. This is satisfactory for the observer.

For the above construction of the second embodiment, in order to display an image of proper size on the TV monitor, it is necessary to satisfy the condition of Eq. (3) already mentioned. Also, where a field mask is placed at the position of the image 8 of the relay optical system 5, the image size Dm stands for the inside diameter of the field mask.

The term $|fi/foc|$ in Eq. (3) implies a magnification obtained by a combination of the eyepiece optical system 6 and the imaging optical system 9. The term $Dm|fi/foc|$ means the size of the rigid-endoscope image 11 projected on the imaging plane. Hence, the value of this term divided by the diagonal length Lc of the effective imaging surface of the image sensor 10 becomes a parameter representing the size of the rigid-endoscope image displayed on the TV monitor. As seen from this, Eq. (3) has the same meaning as Eq. (1) in the first embodiment, and the settings of the upper and lower limits are identical with those explained in reference to FIGS. 2A–2D. Thus, if the value of $Dm|fi/foc|$ is smaller than 0.6, the dark portion in which the image does not exist on the image screen of the TV monitor will increase, with a resulting difficulty in observation. Beyond 1.2, a portion in which the image is not displayed on the image screen increases to raise a problem.

The following tables show numerical data of the optical systems applied to the second embodiment. In these table, C1 and C2 stand for two kinds of samples of the imaging optical system 9 in the second embodiment. Since R1–R6 are the same as in the first embodiment, the data of the rigid endoscope are not shown. Other symbols are the same as those used in Eq. (3). The value of Eq. (3) refers to the value of $Dm|fi/foc|/Lc$.

| Imaging optical system | | | |
|---|---|---|---|
| | Lc (mm) | fi (mm) | Number of pixels |
| C1 | 8.20 | 30.4 | 2,000,000 |
| C2 | 6.42 | 22.0 | 1,200,000 |

| Value of Eq. (3) | | |
|---|---|---|
| | Combination with C1 | Combination with C2 |
| R1 | 0.91 | 0.84 |
| R2 | 1.18 | 1.09 |
| R3 | 0.92 | 0.85 |
| R4 | 0.66 | 0.61 |
| R5 | 1.05 | 0.97 |
| R6 | 0.79 | 0.73 |

As seen from the above explanation, according to the second embodiment, a combination of the rigid endoscope with the imaging device can be arbitrarily selected as in the first embodiment by satisfying the condition of Eq. (3). Moreover, a part or the whole of the imaging optical system, or the image sensor, in contrast with the case of the first embodiment, need not be moved when the field conversion is made, thus doing away with the need for the XY stage and its actuator. Consequently, it is possible for the imaging device to lessen weight, minimize failure, and improve durability.

Comparison of the second embodiment with the first embodiment will show that the image display relative to the low magnification position in the first embodiment corresponds to that relative to all pixels in the second embodiment, while the image display relative to the high magnification position in the first embodiment corresponds to that relative to the partial image trimming in the second embodiment. Thus, in the first embodiment, if it is assumed that the imaging device has the NTSC-grade signal system, the NTSC-grade image quality will be obtained in regard to either the low or high magnification position, and hence good image quality such that the performance of the rigid endoscope is optimized cannot be secured in regard to the low magnification position. In the second embodiment, however, when the image is displayed with respect to all pixels of the image sensor, a signal system of high resolution is used, and thus an image of good quality such that the performance of the rigid endoscope is optimized can be displayed. Furthermore, it becomes possible that the trimmed image for the field conversion has the NTSC-grade image quality.

Although, in the second embodiment, the imaging optical system 9 is constructed with a single focus lens, it may be done with a zoom lens unit. In this case, it is only necessary to satisfy the condition of Eq. (3) in part of the variable magnification limit of the zoom lens unit. Moreover, in the second embodiment, the trimmed image is displayed on the TV monitor 19 by using the NTSC signal processing system 18, but it may be displayed by using a signal system of moderate resolution, such as PAL or Y/C, which is widely used. It is thus possible to display a good image on an inexpensive display. Additionally, in the second embodiment, an image according to full image information derived from the image sensor 10 is displayed through a standard signal of the HDTV system, such as high vision, on the display. However, the display of the HDTV system standard is very expensive at present, and therefore, unless this display is required in particular, the image may be displayed by using the signal system of moderate resolution such as that described above.

Figure 6A:
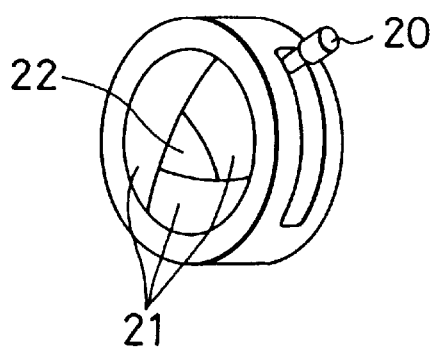
FIGS. 6A and 6B are views for explaining stop mechanisms effectively applied to the first and second embodiments.
Figure 6B:
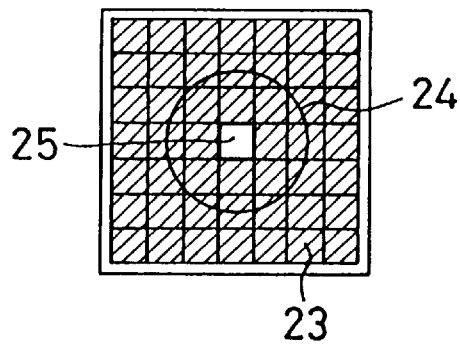

Here, reference is made to modification examples applicable to the first and second embodiments. In either the first or second embodiment, the rigid-endoscope image will be magnified and projected, and as a result, the depth of field tends to decrease. Thus, in order to correct this defect and increase the depth of field, it is favorable that a variable stop mechanism is placed close to a pupil position located on the entrance side of the imaging optical system 9. FIG. 6A illustrates a mechanical, variable stop mechanism suitable for use in this case. This stop mechanism is designed so that, by controlling a stop diameter control pin 20, three stop blades 21 are opened or closed to change the area of a light-transmitting part 22 formed, with the optical axis as its center. Alternatively, as shown in FIG. 6B, a liquid crystal variable stop mechanism may be used which has a plurality of pixels and usually forms a light-blocking part 23. In this case, electrodes arranged in a lattice form are selectively energized and the area of a light-transmitting part 25 of a light beam 24 is changed, with the optical axis as its center.

Figure 7:
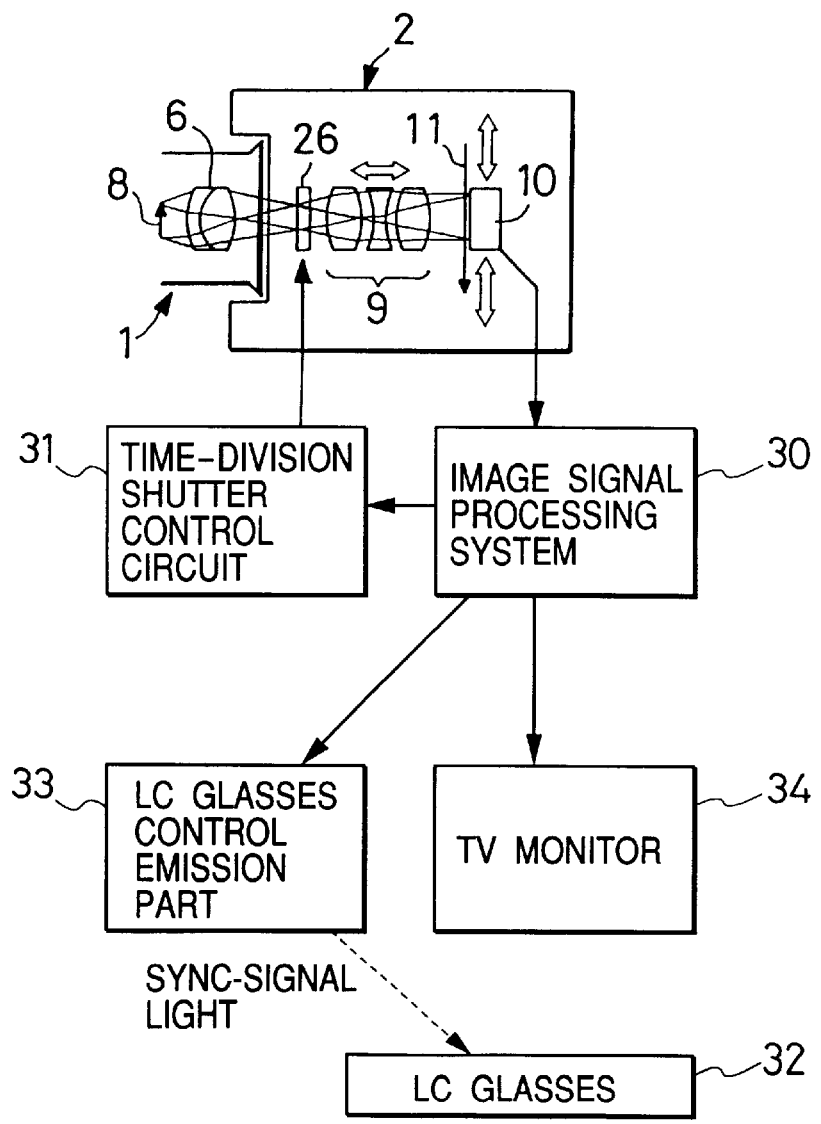
FIG. 7 is a view showing the construction of the field conversion system for rigid endoscopes of a third embodiment in the present invention.
Figure 8A:
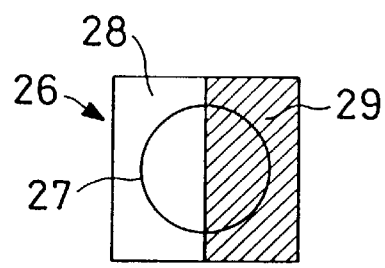
FIGS. 8A and 8B are views for explaining the operation of a liquid crystal time-division shutter used in the third embodiment.

Next, the third embodiment is explained with reference to FIGS. 7, 8A, and 8B. In FIG. 7, the rigid endoscope 1 is identical with that shown in FIG. 1. Thus, like numerals are used in like members, and the rigid endoscope 1 is partially shown. The imaging optical system 2 has the same arrangement as that shown in FIG. 1 with exception that a time-division shutter 26 is placed close to the pupil position of the imaging optical system 9, and thus like numerals are used in like members. For the time-division shutter 26, a mechanical time-division shutter may be used, but the third embodiment uses a liquid crystal time-division shutter which is an optical switching element. FIG. 8A shows the state of the shutter 26 where a light-transmitting part 28 of a light beam 27 is provided on the left side of the optical axis, while a light-blocking part 29 is formed on the right side. Conversely, FIG. 8B shows the state of the shutter 26 where the light-blocking part 29 is on the left side, while the light-transmitting part 28 is on the right side.

Figure 8B:
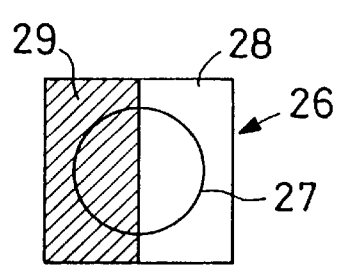

In this way, in the third embodiment, the states of FIGS. 8A and 8B are brought about by the time-division shutter 26, and thereby the light beam 27 in the pupil is separated to lie at different positions in a horizontal direction (to the left and right) of the image sensor 10. Thus, by continuously switching the time-division shutter 26 in agreement with the field or frame frequency of the image sensor 10, two images having parallax in the horizontal direction of the image sensor 10 are acquired time-dividedly in accordance with the field or frame. For the time-division shutter 26, the synchronizing signal of an image signal processing system 30 is used as a trigger and a time-division shutter control circuit 31 outputs a driving signal.

The two images thus available in accordance with the field or frame can be recognized independently by the eyes of the observer, and thereby stereoscopy becomes possible. The third embodiment makes use of liquid crystal glasses 32 for stereoscopy which are well known as a medium thereof, so that an image signal derived from the image signal processing system 30 is allocated by a liquid crystal glasses control emission part 33 and different images are recognized by the eyes. The third embodiment is also designed so that observation can be made by using a TV monitor 34, and the field conversion can be carried out by moving the image sensor 10.

The third embodiment, in which the functions of the field conversion and the stereoscopic observation are thus exercised independently of each other, has advantages that it is possible to carry out the field conversion while making the stereoscopic observation and that a plurality of image sensors are not required. However, when the third embodiment is used, the field conversion may be carried out or surgical treatment may be done, without making the stereoscopic observation. In the entire optical system of the third embodiment, the optical path need not be divided into a plurality of paths by prisms and it is only necessary to consider only the placement of the time-division shutter. This is very convenient for the design of the imaging device. In the third embodiment, as in the first embodiment, if the conditions of Eqs. (1) and (2) are satisfied, a combination of the rigid endoscope 1 and the imaging device 2 can be changed at will.

Figure 9:
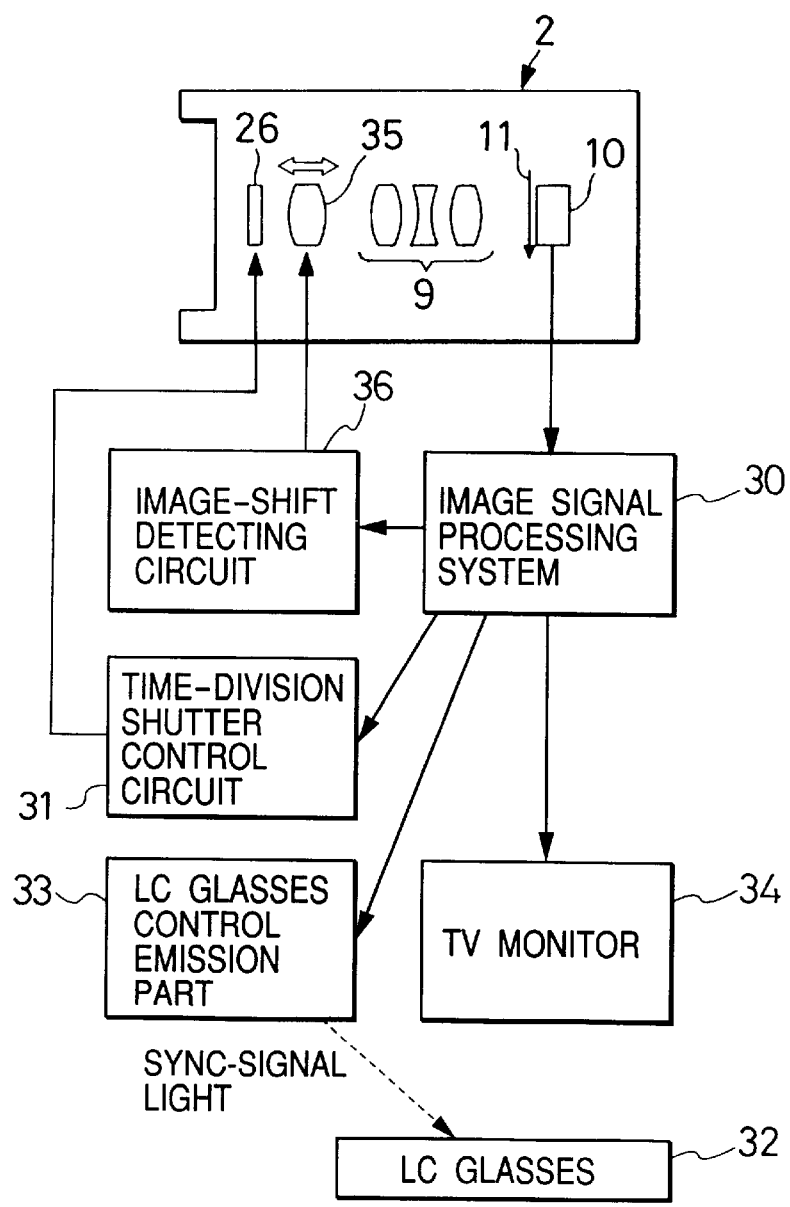
FIG. 9 is a view showing the construction of a modification example of an imaging device in the third embodiment.

When the field conversion is performed, a focus adjustment is sometimes required, and it is desirable that this adjustment is made automatically by an autofocus system. However, a technique that the optical path is divided only for this purpose to detect a phase difference brings about oversizing and high cost of the device and thus is not very favorable. In the imaging device 2 of the third embodiment, however, stereoscopy is possible and hence the use of depth information available here enables the autofocus system to be easily applied. A modification example in such a case is shown in FIG. 9.

In this example, a focus lens 35 is placed to be movable along the optical axis between the time-division shutter 26 and the imaging optical system 9. An image-shift detecting circuit 36 detects an image shift from the image center in a horizontal direction by virtue of a pair of field or frame image signals outputted from the image signal processing system 30, so that the focus lens 35 is moved in accordance with the result of this detection. It is also possible that, without placing the focus lens 35, the image sensor 10 is moved along the optical axis in accordance with the result of the detection of the image-shift detecting circuit 36.

Figure 10:
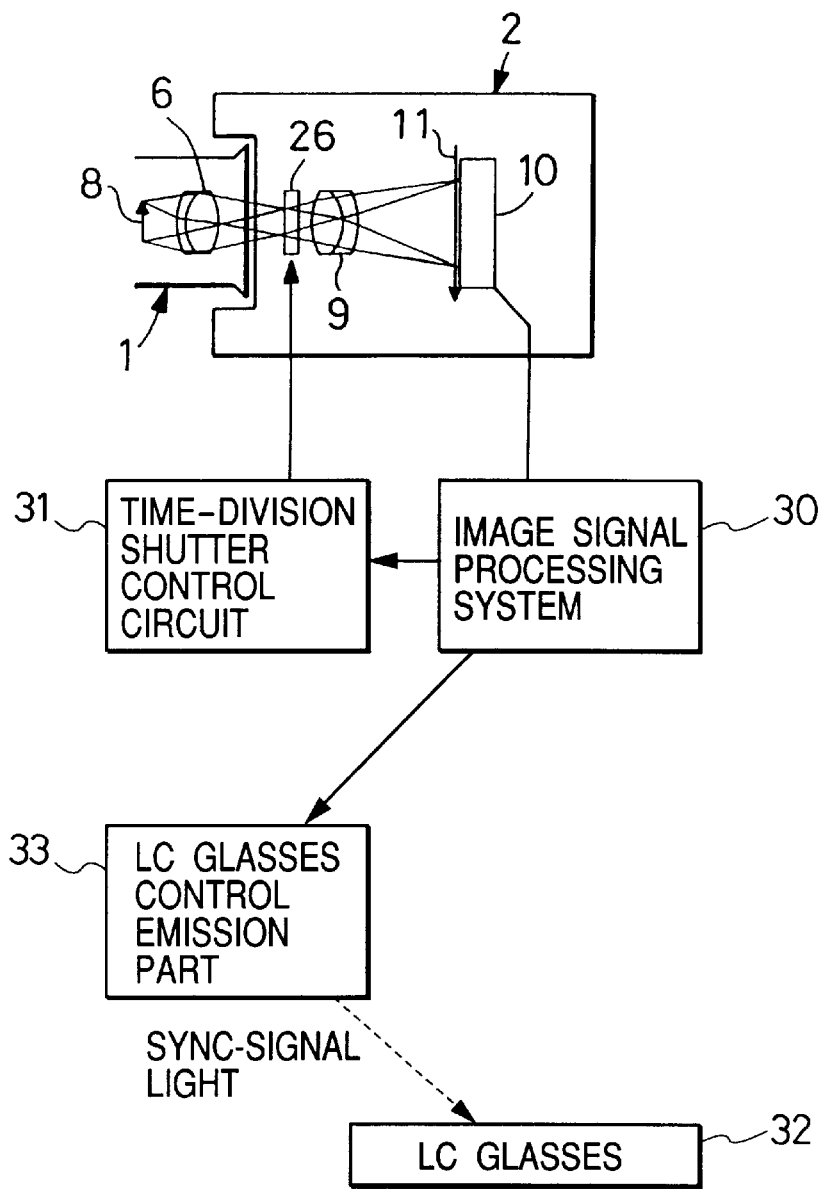
FIG. 10 is a view showing the construction of the field conversion system for rigid endoscopes of a fourth embodiment in the present invention.

Subsequently, the fourth embodiment is described with reference to FIG. 10. This embodiment combines the construction shown in FIG. 5 with the construction for stereoscopic observation explained in the third embodiment. In FIG. 10, like numerals refer to like members and the rigid endoscope 1 is partially shown. Moreover, the members and the like relative to the control and display of the field conversion which are shown in FIG. 5 are omitted from FIG. 10. In this way, since the fourth embodiment does not add any new component, the detailed explanation of its construction is omitted.

According to the fourth embodiment thus constructed, the number of pixels of the image sensor 10 is at least one million, and the stereoscopic observation can be made. Furthermore, the optical system can be designed to satisfy the condition of Eq. (3). It is also possible to have the autofocus function shown in FIG. 9, if necessary. Also, it is needless to say that the function and effect of the same construction, already mentioned, as in the third embodiment are applied to the fourth embodiment.

Here, a description is given of a modification example applica- ble to each of the third and fourth embodiments. In the fourth embodiment, as well as in the third embodiment, the rigid-endoscope image will be magnified and projected, and thus the depth of field tends to decrease as in the first and second embodiments. Thus, in order to correct this defect, as already explained with reference to FIGS. 6A and 6B, it is merely necessary that, in the third and fourth embodiments as well, the variable stop mechanism is placed close to the pupil position located on the entrance side of the imaging optical system 9. In the third and fourth embodiments, however, the liquid crystal shutter is placed, as the time-division shutter 26, close to the pupil position, and thus it is necessary to optimize this shutter.

Figure 11:
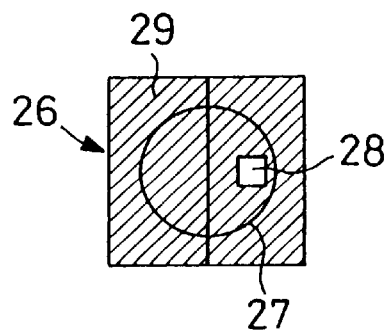
FIG. 11 is a view for explaining a liquid crystal time-division shutter having the function of a variable stop effectively applied to each of the third and fourth embodiments.

Thus, the case where the liquid crystal shutter is used as the time-division shutter 26 and a variable stop function is imparted to this shutter is illustrated in FIG. 11. The shutter 26 shown in FIG. 11 is actuated, as the time-division shutter, as in FIGS. 8A and 8B. Hence, FIG. 11 indicates the same state of actuation as in FIG. 8B. Specifically, the light-blocking part 29 is provided as the shutter on the left side of the optical axis, while the light-transmitting part 28 is on the right side. The light-transmitting part 28 is restricted so that its transmission area diminishes and is designed to function as a stop. Conversely, where the light-transmitting part 28, as shown in FIG. 8A, is provided as the shutter on the left side, the area which is restricted to diminish is formed on the left side, as a matter of course. This aperture restriction of the light-transmitting part 28 may be controlled so that the level of the output from the image sensor 10 is always held constant, or may be controlled in accordance with a change in magnification if the imaging optical system 9 includes a zoom lens unit.

Finally, reference is made to an aspect favorable for the rigid endoscope 1 used in each embodiment. Specifically, it is desirable that the optical system of the rigid endoscope 1 satisfies the following conditions:

$$60° \leq \theta \leq 120° \quad (4)$$

$$0.3 \text{ mm} \leq NA\ Dm \leq 0.9 \text{ mm} \quad (5)$$

Also, where a field mask is placed at the position of the image 8 of the relay optical system 5, the image size Dm stands for the inside diameter of the field mask.

Eq. (4) defines the angle of view of the rigid endoscope for causing the field conversion to function more effectively. If the angle is below 60°, the visual field derived from the rigid endoscope becomes extremely narrow and the rigid endoscope itself must be moved to change the visual field, thus obscuring the meaning of providing the function of the field conversion for labor saving. Beyond 120°, the periphery of the rigid-endoscope image displayed in the field conversion becomes dark, which is unfavorable. It is desirable that whenever the rigid-endoscope image is displayed in the field conversion, the brightness of the image is evenly distributed. Since, however, the distribution of light from the illumination optical system of the rigid endoscope is considerably deteriorated at the place where the angle of view is large, there is a difference in brightness between the middle and the periphery of the rigid-endoscope image to be observed.

A solution of such a problem needs an illumination optical system for bringing about even distribution of light at a wide angle. However, if the angle of view is larger than 120°, it becomes impossible to bring about the even distribution of light. Furthermore, in the case of this angle of view, the problem of distortion will arise. When the field conversion is carried out, the optical system is in a condition of decentering, and therefore if the rigid-endoscope image has distortion, decentering distortion will be produced on the TV monitor. For this reason, an optical design for minimizing distortion produced in an observation optical system becomes necessary, but where the angle of view exceeds 120°, it is extremely difficult to eliminate the distortion. Hence, the angle of view is limited to 120°.

On the other hand, Eq. (5) offers a condition for properly maintaining the brightness and the depth of field which are necessary for the field conversion. The brightness of the observation optical system of the rigid endoscope is proportional to the square of the value of NA Dm, while the depth of field is inversely proportional to the value of NA Dm. In particular, when the field conversion is made, the rigid-endoscope image is magnified. This is disadvantageous with respect to both the brightness and the depth of field. Thus, if the value of NA Dm is below 0.3 mm, the brightness necessary for the field conversion will cease to be maintainable. Beyond 0.9 mm, the depth of field necessary for the field conversion will cease to be maintainable. In either case, the result is unfavorable.

What is claimed is:

1. A field conversion system for rigid endoscopes, comprising:
    a rigid endoscope inserted into an object to be observed, from one end in a longitudinal direction thereof to form an optical image of said object; and
    an imaging device connected to a remaining end of said rigid endoscope;
    said imaging device including:
        an imaging optical system for changing a magnification of said optical image to form a resultant image; and
        an image sensor placed at a position of an imaging plane produced by said imaging optical system,
    a part or a whole of said imaging optical system, or said image sensor being moved in a direction perpendicular to an optical axis, thereby carrying out a field conversion.
    wherein a time-division shutter mechanism is placed close to a pupil position inside said imaging optical system so that two light beams at different positions in a pupil are switched time-dividedly and transmitted and said image sensor picks up time-dividedly left and right images with parallax.

2. A field conversion system for endoscopes, comprising:
    a rigid endoscope inserted into an object to be observed, from one end in a longitudinal direction thereof to form an optical image of said object; and
    an imaging device connected to a remaining end of said rigid endoscope;
    said imaging device including:
        an imaging optical system for forming an image of said optical image; and
        an image sensor placed at a position of an imaging plane produced by said imaging optical system,
    all or a part of image information derived from said image sensor being selectively displayed on a display, thereby performing a field conversion and magnifying and demagnifying an image,
    wherein the number of pixels of said image sensor is set to at least one million,
    wherein a time-division shutter mechanism is placed close to a pupil position inside said imaging optical system so that two light beams at different positions in a pupil are switched time-dividedly and transmitted and said image sensor picks up time-dividedly left and right images with parallax,
    wherein said rigid endoscope includes, in order from said one end thereof, an objective optical system, a relay optical system, and an eyepiece optical system, said relay optical system forming said optical image on a side of said remaining end thereof, and
    wherein said rigid endoscope satisfies the following conditions:

$$60° \leq \theta \leq 120°$$

$$0.3 \text{ mm} \leq NA\ Dm \leq 0.9 \text{ mm}$$

where θ is an angle of view of said rigid endoscope, NA is a numerical aperture of said relay optical system, and Dm is a size of the optical image formed by said relay optical system.

3. A field conversion system for rigid endoscopes according to claim 1, wherein said rigid endoscope includes, in order from said one end thereof, an objective optical system, a relay optical system, and an eyepiece optical system, said relay optical system forming said optical image on a side of said remaining end thereof, and wherein said rigid endoscope satisfies the following conditions:

$$60° \leq \theta \leq 120°$$

$$0.3 \text{ mm} \leq NA\, Dm \leq 0.9 \text{ mm}$$

where $\theta$ is an angle of view of said rigid endoscope, NA is a numerical aperture of said relay optical system, and Dm is a size of the optical image formed by said relay optical system.

4. A field conversion system for rigid endoscopes according to claims 1 or 2, wherein said time-division shutter includes a liquid crystal shutter, said liquid crystal shutter being also actuated as a variable stop.

5. A field conversion system for rigid endoscopes according to claims 1 or 2, wherein a part or a whole of said imaging optical system, or said image sensor is moved along an optical axis to exercise an autofocus function, based on defocus information derived from a calculation process of an amount of shift, at an image center, of left and right images in a stereoscopic observation.

* * * * *